United States Patent
McCormick et al.

(10) Patent No.: US 8,163,565 B2
(45) Date of Patent: Apr. 24, 2012

(54) LIGHT CURING FIXATIVE

(75) Inventors: Patrick McCormick, Rutland, MA (US); James Linder, Acton, MA (US)

(73) Assignee: Cytyc Corporation, Marlborough, MA (US)

( * ) Notice: Subject to any disclaimer, the term of this patent is extended or adjusted under 35 U.S.C. 154(b) by 1750 days.

(21) Appl. No.: 11/297,701

(22) Filed: Dec. 8, 2005

(65) Prior Publication Data

US 2007/0134798 A1 Jun. 14, 2007

(51) Int. Cl.
*G01N 33/00* (2006.01)

(52) U.S. Cl. .................................................. 436/176
(58) Field of Classification Search .................. 422/99, 422/100, 104; 436/180
See application file for complete search history.

(56) References Cited

U.S. PATENT DOCUMENTS

| 4,666,699 A * | 5/1987 | Slifkin ................ 435/40.51 |
| 2002/0086431 A1 * | 7/2002 | Markham et al. ........... 436/63 |

* cited by examiner

*Primary Examiner* — Sam P Siefke

(57) ABSTRACT

The invention relates to a cell fixative that can be used in the preparation of slides for investigation by microscopy techniques. In particular the present invention provides a cell fixative that contains a light curable mounting medium.

1 Claim, No Drawings

LIGHT CURING FIXATIVE

FIELD OF THE INVENTION

The invention relates to a combination of cell fixative and mounting medium that can be used in the preparation of slides for investigation by microscopy techniques. In particular the present invention provides a cell fixative that contains a radiation curable mounting medium.

BACKGROUND OF THE INVENTION

This invention generally relates to the field of the preparation of slides for microscopic review. Cytology is a branch of biology dealing with the study of the formation, structure, morphology, and function of cells. As applied in a laboratory setting, cytologists, cytotechnologists, and other medical professionals make medical diagnoses of a patient's condition based on visual examination of a specimen of the patient's cells. A typical cytological technique is a "pap smear" test, in which cells are scraped from a woman's cervix and analyzed microscopically in order to detect the presence of abnormal cells, a precursor to the onset of cervical cancer. Cytological techniques are also used to detect abnormal cells and disease in other parts of the human body.

Cytological techniques are widely employed because collection of cell samples for analysis is generally less invasive than traditional surgical pathological procedures such as biopsies, whereby a tissue specimen is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. In the processing of tissues for glass slides, the tissues are clinically removed from a patient and placed in a container that often contains a preservative and/or fixative and is then transported to the lab for further treatment or conditioning.

It is generally desirable that the cells on a slide have a proper spatial distribution, so that individual cells can be examined. A single layer of cells is typically preferred. Accordingly, preparing a specimen from a fluid sample containing many cells typically requires that the cells first be separated from each other by mechanical dispersion, fluidic shear, or other techniques so that a thin, monolayer of cells can be collected and deposited on the slide. In this manner, the cytotechnologists can more readily discern abnormal cells. The cells are also able to be counted to ensure that an adequate number of cells have been evaluated. Certain methods and apparatus for generating a thin monolayer of cells on a slide advantageous for visual examination are disclosed in U.S. Pat. No. 5,143,627 issued to Lapidus et al. and entitled "Method and Apparatus for Preparing Cells for Examination;" U.S. Pat. No. 5,240,606 issued to Lapidus et al. and entitled "Apparatus for Preparing Cells for Examination;" U.S. Pat. No. 5,269,918 issued to Lapidus et al. and entitled "Clinical Cartridge Apparatus;" and U.S. Pat. No. 5,282,978 issued to Polk, Jr. et al. and entitled "Specimen Processor Method and Apparatus," all of which are assigned to the assignee of the present invention and all of the disclosures of which are incorporated herein by reference in their entirety.

Once a specimen slide is prepared, the cells can be fixed by either submersing the slide in an alcohol bath or spraying the cells with an alcohol solution. Once fixed, the specimen slide may be stained by manual, semi automated, or automated systems (for example, Dako Autostainer (DakoCytomation Ltd., Ely, United Kingdom). Stained slides are then coverslipped by the application of mounting media which affixes the coverslip to the slide base by the adhesive action of the mounting media.

After being fixed and stained, the specimen may be visually inspected by a cytotechnologists, typically under magnification, and with or without various sources of illumination. Alternatively or additionally, automated machine vision systems have been adapted to aid cytological inspection. For example, an automated vision system may perform a preliminary assessment of the entire slide on which the specimen is disposed to alert the cytotechnologists to potentially the most relevant areas of the slide for close inspection, or may be used to rescreen specimens already analyzed by the cytotechnologists.

Automated specimen processing machines (e.g., ThinPrep® 3000 Processor; Cytyc Corporation, Marlborough, Mass.) prepare microscope slides by transferring cell samples to glass slides. Once the cell samples have been transferred to the slide, the cell sample is fixed through the application of an alcohol solution to the cells. The fixation solution usually contains about 50% ethanol and polyethylene glycol and is applied to the slides in a fine mist. The fixation solution fixes the cells and subsequently evaporates in a short period of time. Although the application of the alcohol based fixation solution in such a manner allows for rapid processing of cell samples, the resultant fine mist of the fixation solution may be spread over a wide area and may result in the accumulation of the fixation solution on other parts of the automated slide processor. Build up of residue of fixation solution is a potential source of instrument error and thus regular maintenance is necessary to keep the slide processor running properly.

Thus, the present invention relates to a cell fixation solution that contains a radiation activated curing polymer that allows a cell sample to be simultaneously fixed and coverslipped.

SUMMARY OF THE INVENTION

The present invention generally relates to a combination cell fixative and mounting medium that can be used in the preparation of slides for investigation by microscopy techniques. In particular the present invention provides a cell fixative that contains a radiation curable mounting medium.

In one embodiment of the present invention, a cell preservative solution comprising a cell fixative in combination with a light curable mounting medium is presented.

In another embodiment of the present invention, a cell preservative solution comprising a cell fixative in combination with an ultra violet curable mounting medium is presented.

In yet another embodiment of the present invention, a method of preparing a microscope slide, the method comprising the steps of; obtaining an analytical specimen composed of cells from a patient, transferring the specimen to a microscopic slide to form a layer of separated cells, and exposing the cells to a cell fixative in combination with a radiation curable mounting medium, is presented.

In still yet another embodiment of the present invention, a method of preparing a microscope slide, the method comprising the steps of obtaining an analytical specimen composed of cells from a patient, transferring said cells to a microscopic slide to form a layer of separated cells, exposing said cells to a fixative solution in combination with a radiation curable mounting medium, applying a coverslip to said slide, and exposing the slide to a radiation source to cure the mounting medium, is presented.

In yet another embodiment of the present invention, a method for preparing a slide, comprising the steps of putting a sample to be investigated onto a slide and exposing the slide to at least one washing step with an alcohol containing an alcohol soluble mounting medium, is presented.

Other objects of the invention will in part be obvious and will in part appear hereinafter.

DEFINITIONS

As used herein, the following terms have the meanings ascribed to them unless specified otherwise.

The term "cell fixative" refers to chemical reagents for the preservation of cell or tissue specimens.

The term "fix" or "fixation" refers to a process to bind, or make firm or stable. The term may be interchangeably used to define both a biochemical process which is used to preserve (fix) the structure of biological material in a state that most closely resembles the structure and/or composition of the original living state, as well as the mechanical process by which biological material (e.g., cells) attaches to a substrate (e.g., microscope slide).

The term "light curable" refers to use ultraviolet light or other radiation sources to initiate curing, which allows a permanent bond without heating.

The term "mounting medium" refers to synthetic organic compounds that are applied to bridge the optical gap between a specimen and a microscope slide and cover glass. Such compounds are capable of being dissolved in alcohol and can be cured and hardened by applying a radiation source such as light, and in particular ultra violet (UV) light.

The term "refractive index" refers to the ratio of the velocity of light in a vacuum to the velocity in some medium. Refractive indices generally increase with the atomic number of the constituent atoms. A high density or high atomic number elements usually results in high refractive indices.

DETAILED DESCRIPTION OF THE INVENTION

The present invention relates to a fixative solution for use in the processing of cell and tissue samples and more particularly relates to a novel combination of agents for use in preparing specimen slides for microscopic evaluation. The present invention generally relates to a combination cell fixative and mounting medium that can be used in the preparation of slides for investigation by microscopy techniques.

It is known in the clinical and research arenas that preservation of cell samples for subsequent analysis is desirable. From a diagnostic standpoint, a specimen is most valuable when it is fresh. The more time that elapses between collection of a specimen and the preparation of a slide or other matrix, the less integrity is retained. As soon as cells are removed from the physiologic conditions of the host, autolysis begins. Properly preserving cellular samples such as cells, cell aggregates and small tissue fragments derived from collections of human or animal tissue is a prerequisite to the accurate diagnosis of disease, especially cancer.

Generally, alcohol solutions, with or without other additives such as polyethylene glycol and formaldehyde, ranging from 50% to 95% (v/v: methanol, ethanol, isopropanol) are known solutions for use in cellular fixation. Alcohol fixatives greater than about 50% (v/v) that are used for collecting and fixing cytologic specimens are not optimum fixatives because the processed cells become distorted in their appearance.

There are commercially available alcohol-based cell fixatives (40-50% (v/v)) on the market. For example, Preserv-Cyt®, (Cytyc Corporation, Marlborough, Mass.), is a methanol-based, buffered, solution designed to support cells during transport and microscope slide preparation with the Thin-Prep® Processor.

Fixatives are needed to preserve cells and tissues in a reproducible and life-like manner. To achieve this, tissue blocks, tissue sections, cell growths, biopsies, lavages, smears, or other collections of cells or tissues are immersed in a fixative fluid. In the case of cells in culture, cell preparations are either submerged or simply air-dried. Fixatives stabilize cells and tissues thereby protecting them from the rigors of subsequent processing and staining techniques. For immunological studies, fixation is especially imperative to ensure the adequacy of the specimen and target antigens. Tissues have differing protein content and structural arrangement, thus they have a variable ability to retain their structure without significant fixation. Incorrect specimen preparation can block or impede antigen labeling in tissue and cells. Examples of cell fixatives are aldehydes (e.g., formaldehyde and glutaraldehyde); oxidizing agents (e.g., osmium tetroxide and chromic acid); and protein-denaturing agents (e.g., acetic acid, methyl alcohol, and ethyl alcohol).

Mounting medium is designed for the permanent preservation of stained cells and tissue sections on microscope slides or other media. Mounting medium are usually synthetic organic compounds that are applied to bridge the optical gap between a specimen and a microscope slide and cover glass. Such compounds are capable of being dissolved in organic solvents such as ethanol, methanol, toluene, xylene, or benzene, and can be cured and hardened by air drying or applying a radiation source (e.g., heat or light). Examples of commercially available mounting medium include, but are not limited to: Permount™ (Fischer Scientific), Eukitt™ (O. Kindler GmbH & Co, Germany), Biomount™ (EMS, Hatfield, Pa.), CureMount™ (Instrumedics, Hackensack, N.J.), and Biomeda™ (Foster City, Calif.).

Light curing adhesives (e.g., ultra violet) are available in a number of chemical systems, most of which are polymer-based. These systems include acrylics and acrylates, epoxies, polyurethanes (PUR), polyesters, silicones, and vinyl and vinyl esters.

In one embodiment of the present invention, a solution comprising a cell fixative in combination with a light curable mounting medium is presented. The combination cell fixative and mounting medium solution contains reagents sufficient to fix cells or tissues as well as polymers that are capable of curing when exposed to light. In a particular embodiment of the present invention, a cell fixative solution comprised of 50-95% alcohol that contains a polymer that cures, when exposed to light, to a refractive index of less than 2.0 is presented.

In another embodiment of the present invention, a cell fixative solution comprised of 50-95% alcohol that contains a polymer that cures, when exposed to ultra violet light, to a refractive index of less than 2.0 is presented.

In yet another embodiment of the present invention, a cell fixative solution comprised of 50-95% alcohol that contains a polymer that cures, when exposed to ultra violet light, to a refractive index of less than 1.5 is presented.

In another embodiment of the present invention, a method of preparing a microscope slide, the method comprising the steps of; obtaining an analytical specimen composed of cells from a patient, transferring the specimen to a microscopic slide to form a layer of separated cells, and exposing the cells to a cell fixative in combination with a radiation curable mounting medium, is presented.

Biological specimens that may be used in the method of the present invention include cells and tissue obtained from cervical smears, the breast, urinary tract malignancies colon, lung, bladder, skin, larynx, oesophagus, bronchus, lymph nodes, and haematological malignancies, also blood and serum for evidence of metastatic sarcoma and carcinoma. The method of the present invention may additionally be used to examine cervical glandular epithelial cells (glandular intra-epithelial neoplasia, GIN) or pre-malignant abnormalities in other tissues including malignancies of glandular cells (eg. lung, breast, colon, prostate, stomach), squamous cells (e.g. lung, skin, oesophagus) or other epithelial cell types (e.g. bladder, urethra, kidney, ovary). Cell or tissue samples may be removed from the body using any convenient means and technique. A spatula or swab may be used to remove endothelium cells, e.g. from the cervix or buccal cavity. Blood and other fluid samples may be removed using a syringe or needle. Other tissue samples may be removed by biopsy or tissue section.

Once the cell sample arrives at the laboratory, the biological material is transferred from the cell sample container and onto a glass microscope slide. An automated processor, such as the ThinPrep® 2000 Processor (Cytyc Corporation, Marlborough, Mass.) may be used to collect cells from the cell sample container and deposit them in a thin layer on a glass slide for analysis. The patient's cells in a preservative fluid in a sample container are dispersed using a spinning sample collector disposed therein. A controlled vacuum is applied to the sample collector to draw the fluid through a screen filter thereof until a desired quantity and spatial distribution of cells is collected against the filter. Thereafter, the sample collector is removed from the sample container and the filter portion impressed against a glass slide to transfer the collected cells to the slide in substantially the same spatial distribution as collected.

Usually, once a slide is prepared, the cellular material undergoes a secondary fixation step. The secondary fixation of cells after a slide is prepared serves to further preserve the cellular contents as well as assisting with the bonding of the cells to the surface of the microscope slide. The fixation of the cells is usually done by either submersing or spraying the cells with an alcohol solution (50-95%). Once fixed, the cells are then stained to make visible one or more of the components of the sample or material, such as cell nuclei, cell cytoplasm, tissue and cell structures. Such staining techniques and reagents may include, for instance, stains such as Hematoxylin and eosin (for histochemistry), immunoperoxidase (immunochemistry), and Papanicolaou (cytology). After the cellular material is stained, excess stain may be removed using one or more washing steps with water, alcohol (ethanol, iso-propyl, or benzyl alcohol), or another suitable reagents. Thereafter, the slides are generally submerged or sprayed with an organic solvent or solvent mixture (e.g., xylene or toluene), before a cover glass is fixated to the slide using a mounting medium.

The combination of a cell fixation solution and a radiation curable mounting medium allows for fewer steps in the processing of cell specimens and also reduces the number of reagents used. Fewer reagents used means reduced cost as well as less waste generated. For automate slide processing, secondary fixation steps are applied to microscope slide by the application of a fine mist of cell fixative. The application of a fine mist potentially results in the accumulation of the fixation solution on other parts of the automated slide processor. Build up of residue of fixation solution is a potential source of instrument error. For example, an automated processor, such as the ThinPrep® 3000 Processor (Cytyc Corporation, Marlborough, Mass.) uses a cell fixation spray composed of approximately 50% ethanol and polyethylene glycol (PEG). The cell fixative cures by drying and thus accumulates over time on the instrument resulting in a sticky film that needs to be removed. The combination of a cell fixation solution and a radiation curable mounting medium would allow for slides to be processed directly from a slide processing instrument to coverslipping in only one step. Any excess fixative that collects on the processor may then be easily removed.

Alternatively, a slide may be processed, stained and coverslipped in a minimum of two steps instead of the usual three or more steps. In another alternative, the staining process may be combined with the secondary fixation and the coverslipping process to combine the usual three slide processing steps into one.

In another embodiment of the present invention, a method of preparing a microscope slide, the method comprising the steps of obtaining an analytical specimen composed of cells from a patient, transferring said cells to a microscopic slide to form a layer of separated cells, exposing said cells to a fixative solution in combination with a radiation curable mounting medium, applying a coverslip to said slide, and exposing the slide to a radiation source to cure the mounting medium, is presented.

In yet another embodiment of the present invention, a method for preparing a slide, comprising the steps of putting a sample to be investigated onto a slide and exposing the slide to at least one washing step with an alcohol containing an alcohol soluble mounting medium, is presented.

The combination cell fixative and mounting medium of the present invention may also be used in the preparation of a specimen for selective staining of a macromolecular species (protein, nucleic acid) or a smaller molecule (protein adduct, drug, metabolite, signal transduction species, lipid, etc.). Analysis of preserved tissue is often performed using an antibody that binds specifically and with high affinity to the analyte in the tissue. For sequence-specific detection of nucleic acids, a detectable complementary oligo- or polynucleotide sequence (probe) can be used for hybridization. Hybridization can be done on intact cell structures (in situ) for cytometric assay (e.g., by microscopy or flow cytometry). A variety of analytical tests can be performed with better sensitivity and quality control when practiced either directly upon biological samples prepared using the present invention, or upon extracts prepared therefrom. These tests comprise the categories of immunoassays (e.g., IHC, flow immunocytochemistry, ELISA, immunoprecipitation, immunoblotting), assays for nucleic acid quantitation and sequence without amplification (e.g. in situ hybridization, quantitation) or with amplification methods (e.g., PCR, in situ PCR, solution PCR, RT-PCR, ligase chain reaction, strand displacement amplification, NASBA), chromatographic methods (e.g., gas or liquid phase analyte transport), electrophoretic methods (capillary, slab gel) photometric methods (e.g., UV or visible or infra-red spectrophotometry, fluorimetry) and other methods for analysis of molecular compositions (e.g., mass spectroscopy, NMR).

The combination cell fixative and mounting medium may contain additional additives that stabilizes fluorochromes and substantially decreases bleaching under UV radiation. This results in prolonged gleaming signals and higher contrast of the images

EQUIVALENTS

Those skilled in the art will recognize, or be able to ascertain using no more than routine experimentation, many equivalents to the specific embodiments of the invention described herein. The invention can be embodied in other specific forms without departing from the spirit or essential characteristics thereof. The present embodiments are therefore to be considered in all respects as illustrative and not restrictive. The scope of the invention is indicated by the appended claims, rather than by the foregoing description, and all changes which come within the meaning and range of equivalency of the claims are therefore intended to be embraced therein.

The invention claimed is:

1. A method of preparing a microscope slide, the method comprising the steps of:

a.) obtaining an analytical specimen composed of cells from a patient,
b.) transferring said cells to a microscopic slide to form a layer of separated cells,
c.) exposing said cells to fixative solution in combination with a radiation curable mounting medium,
d.) applying a coverslip to said cells
e.) exposing said slide to a radiation source to cure said mounting medium.

* * * * *